US010279181B2

(12) United States Patent
Trier et al.

(10) Patent No.: US 10,279,181 B2
(45) Date of Patent: May 7, 2019

(54) MEASURING LOAD IMPEDANCE WITH ACTIVE STIMULATION PULSES IN AN IMPLANTED PULSE GENERATOR

(71) Applicant: Nuvectra Corporation, Plano, TX (US)

(72) Inventors: Stephen C. Trier, Bothell, WA (US); Jeff A. Weisgarber, Jewett, OH (US)

(73) Assignee: NUVECTRA CORPORATION, Plano, TX (US)

( * ) Notice: Subject to any disclaimer, the term of this patent is extended or adjusted under 35 U.S.C. 154(b) by 796 days.

(21) Appl. No.: 14/793,780

(22) Filed: Jul. 8, 2015

(65) Prior Publication Data

US 2015/0306398 A1 Oct. 29, 2015

Related U.S. Application Data

(62) Division of application No. 13/110,466, filed on May 18, 2011, now Pat. No. 9,101,767.

(51) Int. Cl.
*A61N 1/36* (2006.01)
*A61N 1/39* (2006.01)

(52) U.S. Cl.
CPC ....... *A61N 1/36139* (2013.01); *A61N 1/3615* (2013.01); *A61N 1/36071* (2013.01); *A61N 1/36125* (2013.01); *A61N 1/3937* (2013.01)

(58) Field of Classification Search
CPC ............ A61N 1/36071; A61N 1/36125; A61N 1/36139; A61N 1/3615; A61N 1/3937
See application file for complete search history.

(56) References Cited

U.S. PATENT DOCUMENTS 5,895,416 A 4/1999 Barreras, Sr. et al.
6,181,969 B1 1/2001 Gord
(Continued)

FOREIGN PATENT DOCUMENTS

EP 0247649 12/1987
WO WO 00/00251 1/2000
(Continued)

OTHER PUBLICATIONS

European Search Report received in European Application No. 12173231.7, dated Oct. 15, 2012, 6 pages.
(Continued)

*Primary Examiner* — Amanda K Hulbert
(74) *Attorney, Agent, or Firm* — Haynes and Boone, LLP; Eric Li (57) ABSTRACT

The present disclosure provides a medical stimulation system that includes a plurality of implantable channels each operable to obtain a voltage signal from a designated area of a body tissue. The medical stimulation system includes an impedance measurement device. The impedance measurement device includes a plurality of attenuators each coupled to a respective one of the channels. The attenuators are each operable to attenuate an amplitude of the voltage signal received from its respectively-coupled channel. The impedance measurement device includes a multiplexing component that receives the amplitude-attenuated voltage signals from each of the attenuators. The multiplexing component selectively outputs two of the amplitude-attenuated voltage signals. The impedance measurement device includes a differential amplifier that receives the two amplitude-attenuated voltage signals outputted from the multiplexing component as a differential input signal. The differential amplifier generates an amplifier output signal that includes at least partially an amplified version of the differential input signal.

20 Claims, 6 Drawing Sheets

(56) References Cited

U.S. PATENT DOCUMENTS

| | | |
|---|---|---|
| 6,195,585 B1 | 2/2001 | Karunasiri et al. |
| 6,219,580 B1 | 4/2001 | Faltys et al. |
| 6,393,325 B1 | 5/2002 | Mann et al. |
| 6,516,227 B1 | 2/2003 | Meadows et al. |
| 6,553,263 B1 | 4/2003 | Meadows et al. |
| 6,895,280 B2 | 5/2005 | Meadows et al. |
| 7,444,181 B2 | 10/2008 | Shi et al. |
| 7,493,404 B2 | 2/2009 | Weber |
| 7,622,988 B2 | 11/2009 | Denison et al. |
| 7,747,318 B2 | 6/2010 | John et al. |
| 7,769,462 B2 | 8/2010 | Meadows et al. |
| 7,801,615 B2 | 9/2010 | Meadows et al. |
| 7,805,197 B2 | 9/2010 | Bradley |
| 7,831,307 B1 | 11/2010 | Moffitt |
| 8,874,219 B2 | 10/2014 | Trier et al. |
| 8,996,115 B2 | 3/2015 | Trier et al. |
| 8,996,117 B2 | 3/2015 | Trier et al. |
| 2001/0031909 A1 | 10/2001 | Faltys et al. |
| 2005/0187591 A1 | 8/2005 | Carter et al. |
| 2005/0267546 A1 | 12/2005 | Parramon et al. |
| 2006/0004295 A1 | 1/2006 | Prydekker |
| 2007/0156203 A1 | 7/2007 | Varrichio et al. |
| 2008/0058901 A1 | 3/2008 | Ternes |
| 2008/0269630 A1 | 10/2008 | Denison et al. |
| 2009/0082691 A1 | 3/2009 | Denison et al. |
| 2010/0069768 A1 | 3/2010 | Min et al. |
| 2010/0114202 A1 | 5/2010 | Donofrio et al. |
| 2010/0204766 A1 | 8/2010 | Zdeblick et al. |
| 2010/0280577 A1 | 11/2010 | Roy et al. |
| 2012/0277822 A1 | 11/2012 | Trier |

FOREIGN PATENT DOCUMENTS

| | | |
|---|---|---|
| WO | WO 2007/127443 A2 | 11/2007 |
| WO | WO 2010/033610 A1 | 3/2010 |
| WO | WO-2010/055421 | 5/2010 |
| WO | WO 2010/065761 A2 | 6/2010 |
| WO | WO 2011/014909 A1 | 2/2011 |
| WO | WO 2012/088482 A1 | 6/2012 |

OTHER PUBLICATIONS

European Search Report received in European Patent Application No. 12166020.3, dated Sep. 27, 2012, 5 pages.

European Patent Office, European Extended Search Report, Application No. 12166020.3, dated Jul. 25, 2014, 11 pages.

MEASURING LOAD IMPEDANCE WITH ACTIVE STIMULATION PULSES IN AN IMPLANTED PULSE GENERATOR

PRIORITY DATA

The present application is a divisional application of U.S. patent application Ser. No. 13/110,466, filed on May 18, 2011, the disclosure of which is hereby incorporated by reference in its entirety.

BACKGROUND

As medical device technologies continue to evolve, neurostimulator devices have gained much popularity in the medical field. Neurostimulator devices are typically battery-powered devices that are designed to deliver electrical stimulation to a patient. Through proper electrical stimulation, the neurostimulator devices can provide pain relief for patients.

A typical neurostimulator device may include one or more integrated circuit chips on which the control circuitry and neurostimulation circuitry are built. The neurostimulator device may also include a plurality of channels. These channels include respective electrodes that are in contact with different tissue areas of a patient's body. Controlled by the control circuitry, the electrodes are each capable of delivering electrical stimulation to their respective target contact areas. Thus, the patient can use the neurostimulator device to stimulate areas in a localized manner.

Typically, neurostimulator devices have the ability to measure the impedance between channels to monitor the health and operation of the lead wires and electrodes, as well as the impedance of the tissue. Usually, existing neurostimulator devices have to be put into a diagnostic mode in order to make impedance measurements. While in this diagnostic mode, active stimulation is suspended. Measuring impedance in the diagnostic mode may cause several problems, which include delayed detection of component failure, pain or discomfort to the patient, or inaccurate measurement results.

Therefore, while existing neurostimulator devices have been generally adequate for their intended purposes, they have not been entirely satisfactory in every aspect.

SUMMARY

One of the broader forms of the present disclosure involves a medical stimulation system. The medical stimulation system includes a plurality of implantable channels that are each operable to obtain a voltage signal from a designated area of a body tissue while a stimulation pulse is being generated; and an impedance measurement device that includes: a plurality of attenuators that are each coupled to a respective one of the channels, each attenuator being operable to attenuate an amplitude of the voltage signal received from its respectively-coupled channel; a multiplexing component that receives the amplitude-attenuated voltage signals from each of the attenuators, the multiplexing component selectively outputting two of the amplitude-attenuated voltage signals; and a differential amplifier that receives the two amplitude-attenuated voltage signals outputted from the multiplexing component as a differential input signal, the differential amplifier generating an amplifier output signal that includes at least partially an amplified version of the differential input signal.

Another one of the broader forms of the present disclosure involves a medical stimulation device. The medical stimulation device includes an impedance measurement device that is operable to measure impedance of a selected region of a body tissue, the impedance measurement device including: attenuation circuitry that is operable to receive a plurality of voltage signals as inputs and that is operable to generate amplitude-reduced versions of the received voltage signals as outputs; multiplexing circuitry that is operable to receive the outputs of the attenuation circuitry as inputs and that is operable to selectively route a subset of its inputs through as outputs; and amplification circuitry that is operable to receive the outputs of the multiplexing circuitry as a differential input and that is operable to amplify the differential input as an amplifier output.

Yet one more of the broader forms of the present disclosure involve a medical stimulation device. The medical stimulation device includes an impedance measurement means for measuring impedance of a selected region of a body tissue during active stimulation of the tissue, the impedance measurement means including: attenuation means for reducing an amplitude of a plurality of voltage signals; multiplexing means for selectively routing a subset of the amplitude-reduced voltage signals; and amplification means for differentially amplifying the subset of the amplitude-reduced voltage signals.

One more of the broader forms of the present disclosure involves a method. The method includes: electrically stimulating a selected region of a body tissue; obtaining a plurality of voltage signals from designated parts of the body tissue while the selected region of the body tissue is being electrically stimulated; attenuating a voltage amplitude of at least some of the voltage signals, thereby generating amplitude-attenuated voltage signals; selecting a subset of the amplitude-attenuated voltage signals to be amplified; amplifying the subset of the amplitude-attenuated voltage signals differentially to generate an amplifier output; and determining an impedance associated with the selected region of the body tissue based on the amplifier output.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the following disclosure provides many different embodiments, or examples, for implementing different features of the invention. Specific examples of components and arrangements are described below to simplify the present disclosure. These are, of course, merely examples and are not intended to be limiting. Various features may be arbitrarily drawn in different scales for simplicity and clarity.

Figure 1:
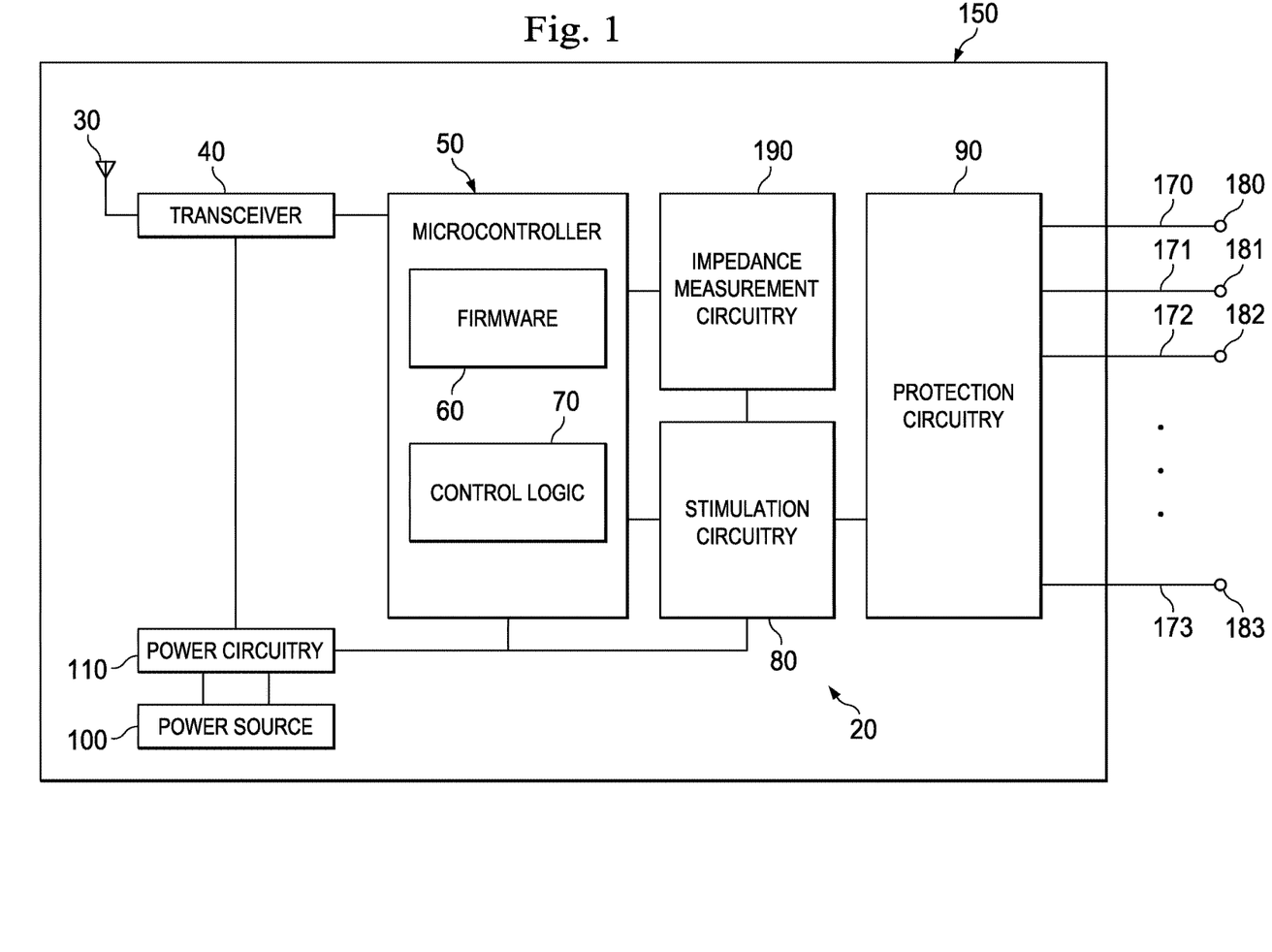
FIG. 1 is a simplified diagrammatic view of an embodiment of a neurostimulator device.

FIG. 1 is a simplified diagrammatic view of an embodiment of a neurostimulator device 20. The neurostimulator device 20 includes an antenna 30 and a transceiver 40 coupled to the antenna 30. The antenna 30 is capable of sending signals to an external device and receiving signals from the external device. The transceiver 40 contains transmitter circuitry and receiver circuitry that together carry out bidirectional digital communication with the external device. In an embodiment, the signals are transmitted and received at Radio Frequencies (RF).

The neurostimulator device 20 includes a microcontroller 50 that is coupled to the transceiver 40. Based on the output of the transceiver 40 (i.e., the input received from the external device), the microcontroller 50 runs firmware 60, which is a control program, to operate control logic 70. The firmware 60 includes dedicated low-level software code that is written for a specific device, in this case the control logic 70. The control logic 70 includes digital circuitry that is implemented using a plurality of transistors, for example Field Effect Transistors (FETs). In the embodiment shown in FIG. 1, the firmware 60 and the control logic 70 are integrated into the microcontroller 50. In alternative embodiments, the firmware 60 or the control logic 70 may be implemented separately from the microcontroller 50.

The neurostimulator device 20 includes stimulation circuitry 80 that receives the output of the microcontroller 50. In an embodiment, the stimulation circuitry 80 is implemented on an Application Specific Integrated Circuit (ASIC) chip. The stimulation circuitry 80 includes electrical pulse generation circuitry. Based on the output of the microcontroller 50, the electrical pulse generation circuitry generates electrical pulses (signals) to a target tissue area. Various aspects of the pulse generation are described in detail in U.S. patent application Ser. No. 13/081,896, Titled "Charge Balancing For Arbitrary Waveform Generator & Neural Stimulation Application" and filed on Apr. 7, 2011, U.S. patent application Ser. No. 13/082,097, Titled "Arbitrary Waveform Generator & Neural Stimulation Application With Scalable Waveform Feature" and filed on Apr. 7, 2011, and U.S. patent application Ser. No. 13/081,936, Titled "Arbitrary Waveform Generator & Neural Stimulation Application" and filed on Apr. 7, 2011, each of which is hereby incorporated by reference in its entirety.

The neurostimulator device 20 also includes protection circuitry 90 that is coupled to the output of the stimulation circuitry 80. In an embodiment, the protection circuitry 90 includes direct-current (DC) blocking capacitors and other electrical transient suppression components. The protection circuitry 90 protects the patient's tissue from unwanted electrical signals. The protection circuitry 90 also protects the neurostimulator device 20 from undesirable external electrical signals that may be generated by events such as electrostatic discharge, defibrillation, or electrocautery.

The neurostimulator device 20 also includes a power source 100 and power circuitry 110. In an embodiment, the power source 100 includes a battery. In another embodiment, the power source 100 includes a coil that is a part of a transformer (not illustrated). In that case, the transformer has a charging coil that is external to the neurostimulator device 20 and inductively coupled to the coil of the power source 100. The power source 100 therefore obtains energy from such inductive coupling to the charging coil. In some embodiments, the power source 100 may also include both a battery and a coil. The power source 100 provides electrical power to the power circuitry 110. The power circuitry 110 is coupled to the transceiver 40, the microcontroller 50, and the stimulation circuitry 80. The power circuitry 110 supplies and regulates power to these coupled circuitries. In an embodiment, the power circuitry 110 is implemented on an ASIC device.

In an embodiment, the antenna 30, the transceiver 40, the microcontroller 50, the stimulation circuitry 80, the protection circuitry 90, the power source 100, the power circuitry 110, and an impedance measurement circuitry 190 (discussed below) are all contained within a hermetically-sealed housing or can 150, which may also be considered a part of the neurostimulator device 20. The housing 150 may be made from titanium or another suitable durable and/or conductive material that is compatible with human implantation.

A plurality of conductors (also referred to as lead wires) 170-173 run from the internal circuitry through hermetic feedthroughs to one or more connectors mounted on the hermetic enclosure. The lead wires 170-173 plug into, and are removable from, those connectors. In another embodiment, the connectors are eliminated, and the lead wires 170-173 are directly and permanently connected to the hermetic feedthroughs. In some embodiments, the neurostimulator incorporates the electrode contacts into its outer surface. In such embodiments, the hermetic feedthroughs may be designed to incorporate an electrode contact in the tissue-facing side of each feedthrough, or may be designed to have insulated lead wires built into the neurostimulator housing, exterior to the hermetically-sealed enclosure, that carry signals between the hermetic feedthroughs and the electrode contacts. It is understood that the lead wires 170-173 are shown here merely as examples, and that an alternative number of lead wires may be implemented, for example 16 or 24 lead wires.

Electrode contacts 180-183 (also referred to as electrodes) are coupled to the lead wires 170-173. The electrode contacts 180-183 are implanted in different areas of a patient's body, where electrical stimulation is desired. These different areas may be within a few inches of one another. In an embodiment, an exterior portion of the housing 150 is also used as an electrode contact. In another embodiment, one or more electrode contacts can be incorporated into the design of a non-conductive housing 150. In any case, the electrode contacts may also be considered parts of the neurostimulator system.

In an embodiment, the neurostimulator device 20 is implemented as an Implanted Pulse Generator (IPG) having all the components shown in FIG. 1 that is surgically implanted inside the patient's body. Outside the body, the neurostimulator device 20 can be programmed using a Clinician Programmer (not illustrated) or a Patient Programmer (not illustrated). The Clinician Programmer is used by medical personnel to configure the neurostimulator device 20 for the particular patient and to define the particular electrical stimulation therapy to be delivered to the target area of the patient's body. The Patient Programmer is used by the patient himself to control the operation of the neurostimulator device 20. For example, the patient can alter one or more parameters of the electrical stimulation therapy, depending on the programming and the configuration of the neurostimulator device 20 as set by the Clinician Programmer.

In alternative embodiments, the neurostimulator device 20 can be implemented as an External Pulse Generator (EPG). In that case, only a portion of the neurostimulator system (for example the electrode contacts 180-183 and/or portions of the lead wires 170-173) is implanted inside the patient's body, while the neurostimulator device 20 remains outside the body. Other than their exact placements, the functionalities and the operations of the IPG and the EPG are similar. Thus, in the following discussions, IPG may be used to refer to both an IPG and an EPG. A medical device manufacturer may manufacture and provide the neurostimulator device 20 to a clinician or a patient. Clinicians may also provide the neurostimulator device to a patient. Some of the functionalities of the microcontroller 50 may be pre-programmed by the manufacturer or may be programmed by the clinician or patient.

The neurostimulator device 20 is capable of varying the amount of electrical stimulation delivered to each of the electrode contacts 180-183. This is carried out by creating individually controllable electrical paths, or channels. Each channel includes one of the electrode contacts 180-183, one of the lead wires 170-173 coupled to the electrode contact, and respective portions of the protection circuitry 90 and respective portions of the stimulation circuitry 80.

The impedance between any two channels includes impedance contributions from the lead wires (such as lead wires 170-173), the electrode contacts (such as the electrode contacts 180-183), and the patient's body tissue coupled in between these channels. Other contributors to the impedance may include the protection circuitry 90 and the connector for the lead wires, if they are detachable. This impedance includes a complex component that may be inductive, capacitive, or a combination thereof. If the impedance is monitored during typical therapeutic stimulation, then problems (such as breakages) related to the lead wires or electrode contacts can be promptly discovered, as they are typically correlated with a change in impedance between the channels. Also, a change in impedance between channels may signify body tissue damage (such as scarring) or the electrode contacts shifting position inside the patient's body. These events may require stimulation adjustment.

Traditional neurostimulator devices use a diagnostic mode to carry out such impedance measurements. Active stimulation is suspended before the neurostimulator device is put into the diagnostic mode, where low amplitude test signals (typically lower than the stimulation signals) are used to measure the impedance between channels. This traditional method of measuring impedance has several problems. First, if a problem occurs with the lead wires, electrode contacts, or the body tissue during normal active stimulation, the problem cannot be immediately detected by the neurostimulator. Consequently the patient may be over-stimulated or under-stimulated for a period of time until the problem is detected. Second, putting the neurostimulator in the diagnostic mode means active stimulation is ceased. The cessation of stimulation exposes the patient to the pain again (i.e., pain that was previously alleviated by the stimulation). In addition, the electrical signals used by the diagnostic test may cause pain or discomfort to the patient during the diagnostic test. Third, the impedance measurement may not be very accurate. This is partially due to the fact that the charge-transfer function of the electrode-tissue interface can vary as a function of amplitude. As a result, the impedances that are measured with low amplitude pulses used in the diagnostic test are not the same as the impedances that are measured with high amplitude pulses used during active stimulation. Since the measured impedance may be inaccurate, it is difficult to adjust the stimulation parameters appropriately.

The neurostimulator device 20 overcomes the problems associated with existing neurostimulator devices by including impedance measurement circuitry 190 that can measure impedance between channels during active electrical stimulation. In one embodiment, the impedance measurement circuitry 190 is implemented separately from, but coupled to, the stimulation circuitry 80. The impedance measurement circuitry 190 is also coupled to the microcontroller 50. The impedance measurement circuitry 190 receives operating instructions from the microcontroller 50 and feeds readings or measurement results back to the microcontroller 50. The impedance measurement circuitry 190 may be implemented inside or outside the hermetically-sealed housing 150. In another embodiment, the impedance measurement circuitry 190 is implemented on the same application-specific integrated circuit (ASIC) as the stimulation circuitry 80. In yet another embodiment, some elements of the impedance measurement circuitry 190 are implemented with the stimulation circuitry 80 while other elements are implemented on the microcontroller 50.

Figure 2:
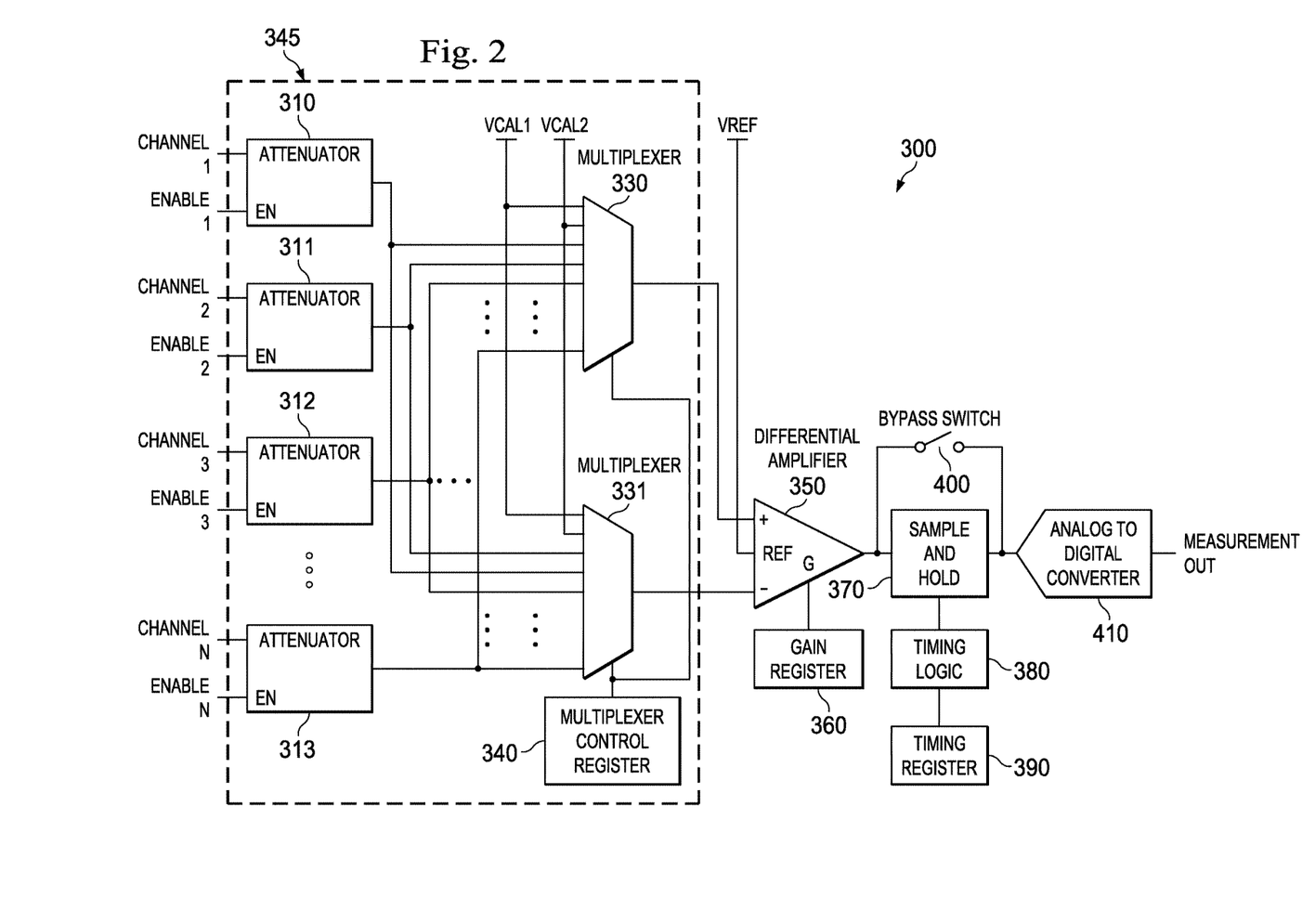
FIG. 2 is a simplified circuit level view of an embodiment of an impedance measurement device.

FIG. 2 shows a simplified diagrammatic view of an impedance measurement device 300 that is an implementation of the impedance measurement circuitry 190 of FIG. 1 according to one embodiment. The impedance measurement device 300 includes an impedance measurement circuit and therefore may also be referred to as an impedance measurement circuit. The impedance measurement device 300 includes several stages. The first stage is an attenuation stage that includes a plurality of attenuators, four of which are illustrated as 310-313. The attenuators are coupled to channels 1, 2, 3, and N, respectively. It is understood that a plurality of additional attenuators may be coupled to other channels, but they are not shown here for reasons of simplicity. Also, one or more of the channels coupled to the attenuators 310-313 may be inactive.

One of the functions of the attenuators 310-313 is to reduce the voltage outputs from their respective channels to a lower voltage that can be easily handled by the rest of the circuitry of the impedance measurement device 300. To accomplish the voltage reduction, in an embodiment the attenuators 310-313 each include a plurality of resistors which form a resistive-divider structure (also known as a voltage divider).

Figure 4:
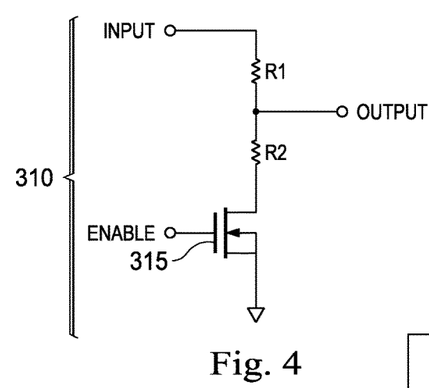
FIG. 4 is a simplified circuit level view of an embodiment of an attenuator device shown in FIGS. 2-3.

An example attenuator utilizing the resistive-divider structure is illustrated in FIG. 4. Referring to FIG. 4, the example attenuator 310 includes resistors R1 and R2. The values of R1 and R2 can be chosen in a manner to achieve the desired amount of voltage reduction. Here, the resistor R1 is coupled to the resistor R2 in series, where R1 is also coupled to its respective channel, and R2 is coupled to a transistor 315, which acts as a switch (discussed in more detail below). The output of the attenuator is taken from the node where R1 and R2 are coupled together. Thus, the output voltage of the attenuator=input voltage of the attenuator*[R2/(R1+R2)]. In an embodiment, R1=2.7 Mega-ohms, and R2=300 Kilo-ohms. Thus, the output voltage of the attenuator=input voltage of the attenuator*[0.3/(2.7+0.3)] =0.1*input voltage of the attenuator. In this manner, a channel output voltage as high as 23 volts or more (which is the input voltage of the attenuator) can be reduced down to a few volts (2.3 according to the example above) by each of the attenuators 310-313. Thus, the attenuators 310-313 effectively help to ensure the proper functioning of the impedance measurement device 300 even when the neurostimulator device 20 is being used at high electrical stimulation levels.

In addition, because an attenuator permanently attached to ground would needlessly shunt current away from the tissue, hence wasting power and shortening the time between battery charges, an enable input is used to turn on and off the attenuator. The transistor 315 in FIG. 4 functions as a switch, controlled by the Enable input. When the Enable input is sufficiently above ground, the transistor 315 is switched "on", that is, to a low-resistance state, and the attenuator is enabled. When the Enable input is grounded, the transistor 315 is switched "off", that is, to a very high resistance state, and the attenuator is disabled. The dimensions of the transistor 315 are chosen to provide a resistance much lower than R1, preferably less than 0.01*R1, when it is switched "on". The dimensions are also chosen to maintain an relatively low capacitance from source to drain when it is switched "off".

It is understood that alternative implementations of the attenuator circuits are possible too. For example, another way to implement the attenuator includes a cascade of a log and antilog circuit. By arranging for an offset or subtraction between the stages, or a suitable scaling of transistor dimensions, the output voltage will closely approximate the input voltage divided by an attenuation factor.

The amount of attenuation provided by the attenuator circuits may be fixed or may be selectable from among several possibilities. Having multiple possible amounts of attenuation may help overcome limitations of the differential amplifier (discussed below) and increase the range of stimulation amplitudes and tissue impedances over which accurate results may be obtained.

Referring back to FIG. 3, one aspect of the attenuators 310-313 is that they have a high input impedance compared to the impedances to be measured, because any current that flows from the stimulation circuitry through the tissue will be reduced by the attached impedance-measurement attenuator, possibly affecting the accuracy of the stimulation amplitude. For example, if resistor dividers are used to implement the attenuators 310-313, the resistances must be sufficiently high that they do not significantly reduce the current delivered to the tissue. In an embodiment, it may be beneficial to remove the ability to selectively enable the attenuators.

Each of the attenuators 310-313 has an enable input (EN) to allow the respective attenuator to be turned on while impedance measurements are being made, and turned off when the attenuator is not needed. The enable inputs receive Enable signals from a control device, for example the microcontroller 50 of FIG. 1. Thus, the attenuators 310-313 may be selectively turned on or off in a manner so that only some of the voltage signals from their respectively-coupled channels are reduced.

The impedance measurement device 300 includes a multiplexing stage after the attenuation stage. In the embodiment shown in FIG. 2, the multiplexing stage includes two multiplexers 330 and 331. In other embodiments, the multiplexing stage may include a single multiplexer or more than two multiplexers. In the embodiment shown in FIG. 2, low-voltage multiplexers are used to implement the multiplexing stage. In another alternative embodiment, high-voltage multiplexers can be used to implement the multiplexing stage. In that embodiment, the multiplexing stage can be implemented before the attenuation stage. Consequently, only two attenuators need to be implemented. This alternative embodiment will be discussed below in more detail with reference to FIG. 3.

Still referring to FIG. 2, each of the multiplexers 330-331 receives the outputs of all the attenuators 310-313 as inputs to the multiplexer. In other words, the outputs of the attenuators 310-313 are coupled to the inputs of the multiplexer 330, as well as to the inputs of the multiplexer 331. In addition, each of the multiplexers 330-331 has an enable line (not illustrated) that allows the multiplexer to be enabled during a measurement and disabled when not needed.

Furthermore, the multiplexers 330-331 each receive one or more calibration voltages as inputs. In the embodiment shown, the multiplexers 330-331 each receive calibration voltages $V_{cal1}$ and $V_{cal2}$. The purpose of the calibration voltages $V_{cal1}$ and $V_{cal2}$ is that a known voltage level can be applied to the subsequent circuitry blocks of the impedance measurement device 20 before real impedance measurements begin. This allows the functionality of the impedance measurement circuitry to be checked. For example, when $V_{cal1}$ and $V_{cal2}$ are set to the same value for both multiplexers 330-331, errors associated with voltage offsets of the multiplexers and the later stage circuitry can be ascertained. When $V_{cal1}$ and $V_{cal2}$ are set to different values for the multiplexers 330-331, the overall gain through the impedance measurement device 300 can be measured. In this manner, the impedance measurement device 300 can be properly calibrated to obtain better measurement accuracy. It is understood that in some alternative embodiments, only a single calibration voltage is used to carry out calibration. In another embodiment, $V_{cal1}$ and $V_{cal2}$ are not variable. Instead, they may have fixed voltages derived from a stable reference-voltage circuit, such as a classic bandgap reference circuit. To calibrate out offset, both multiplexers are set to either $V_{cal1}$ or $V_{cal2}$. Thus, they are inherently seeing the same voltage on their inputs, and the offset error of the multiplexers and later stages can be measured. Using fixed voltages for $V_{cal1}$ and $V_{cal2}$ may improve the accuracy of the calibration.

The multiplexers 330-331 each return a single output in response to a multiplexer control register 340. The multiplexer control register 340 is a part of, or may be controlled by, the microcontroller 50 of FIG. 1. The multiplexer control register outputs a control signal that instructs the multiplexers 330-331 to route a particular one of its inputs (the reduced channel output voltages) to the output of the multiplexers. Thus, depending on the value of the control signal from the multiplexer control register 340, reduced output voltages from selected channels can be outputted by the multiplexers 330-331 and thus used for impedance measurements. For example, if the impedance between channel 1 and channel 2 needs to be measured, the multiplexer control register 340 will instruct the multiplexers 330 and 331 to route the output of channel 1 and channel 2 to the multiplexer outputs, respectively, which will be processed by circuitry in the later stages of the impedance measurement device 300.

The attenuation stage (containing the attenuators 310-313) and the multiplexing stage (containing the multiplexers 330-331) may collectively be referred to as a first stage circuitry 345. The remaining circuitry that comes after the first stage circuitry 345 may be collectively referred to as a second stage circuitry. As discussed above, the order of whether the attenuation stage is implemented before the multiplexing stage (or vice versa) is not important. In the embodiment shown in FIG. 2, the multiplexers 330-331 are low voltage multiplexers which typically cannot handle the entire range of the voltage signals outputted from the channels. In an embodiment, the voltage range that these low voltage multiplexers 330-331 can tolerate is from about 0 volts to about 2.5 volts. In alternative embodiments, these multiplexers 330-331 can handle an input voltage range as low as 0-1 volts or as high as 0-5 volts. Due to the low input voltage range, the attenuation stage needs to be placed before the multiplexing stage in the embodiment shown in FIG. 2. Another embodiment will be discussed below in which the multiplexers are high voltage multiplexers and therefore can be implemented before the attenuation stage.

Still referring to FIG. 2, the impedance measurement device 300 also includes an amplifying stage after the multiplexing stage. In the embodiment shown, the amplifying stage includes a differential amplifier 350 that receives the outputs of the multiplexers 330-331 as its two differential inputs. The differential amplifier 350 will amplify (or magnify) the differential input voltage into a larger amplifier output voltage. In one embodiment, the amplifier 350 amplifies the input voltage differentially and generates a differential output. In another embodiment, the amplifier 350 amplifies the input voltage in a single ended manner.

The amount of magnification is referred to as gain. Hence, if the input differential voltage is magnified 100 times as an amplifier output voltage, the gain is 100 times, or 20 dB in decibels. The desired amount of gain of the differential amplifier 350 can be programmably set by a gain register 360, which is a part of (or controlled by) the microcontroller 50 of FIG. 1. During stimulation with low amplitude pulses, the voltage differential between the channels can be small, and thus the gain of the differential amplifier 350 will be set sufficiently high to allow for an accurate measurement. For high amplitude stimulation, the voltage differential will be large, and thus the gain of the differential amplifier 350 will be set sufficiently low to avoid driving the differential amplifier output to one of its rails.

The differential amplifier 350 also receives a voltage reference input $V_{ref}$. In an embodiment, $V_{ref}$ is set to a value that is equal to about ½ of the input range of an Analog-to-Digital Converter (ADC) 410 that is in a later stage (the ADC 410 will be discussed in more detail later). For example, in an embodiment where the ADC in the later stage has an input range from 0-2.5 volts, $V_{ref}$ is set to 1.25 volts. The amplifier output voltage is offset from ground by the reference voltage $V_{ref}$. In other words, the amplitifer output voltage is equal to the differential voltage at the input of the differential amplifier multiplied by the gain and then summed with the reference voltage $V_{ref}$. Thus, if the differential voltage at the input of the differential amplifier 350 is positive, then the output voltage of the differential amplifier 350 has a value greater than $V_{ref}$ (>1.25 V in this case). On the other hand, if the differential voltage at the input of the differential amplifier 350 is negative, then the output voltage of the differential amplifier 350 has a value less than $V_{ref}$ (<1.25 V in this case). Therefore, the amplifier output voltage from the differential amplifier 350 is centered around the reference voltage $V_{ref}$. In this manner, the amplifier output voltage can stay within the input range of the ADC and still have maximum room to swing in either direction before being "clipped."

The impedance measurement device 300 further includes a sample-and-hold stage (S/H stage). The S/H stage includes a sample-and-hold circuit (S/H circuit) 370 that is coupled to the output of the differential amplifier 350. The S/H circuit 370 measures an instantaneous value (e.g. takes a sample) of the amplifier output voltage from the differential amplifier 350 at a precise time. Once a sample has been taken, the S/H circuit 370 will maintain the sampled voltage until it has been cleared by the firmware 60 of the microcontroller 50 of FIG. 1. The S/H stage also includes a timing logic 380 and a timing register 390. The timing register 390 may be a part of (or controlled by) the microcontroller 50 of FIG. 1 and controls the timing logic 380. The timing logic 380 governs the timing of the sampling performed by the S/H circuit 370. Specifically, the timing logic 380 allows the S/H circuit 370 to sample the amplifier output voltage at one or more precise points in time either during the stimulation phase or during a recovery phase that follows the stimulation phase.

The S/H stage also includes a bypass switch 400 that allows the amplifier output voltage from the differential amplifier 350 to bypass the S/H circuit 370 and be fed directly into an Analog-to-Digital Converter 410. The ADC 410 is the ADC discussed above, whose input range is twice the value of the reference voltage $V_{ref}$. In an embodiment, the ADC 410 has its own built-in sampling circuitry. In another embodiment, the ADC 410 does not have built-in sampling circuitry. The ADC 410 converts the analog voltage from either the S/H circuit 370 (if the S/H circuit is not bypassed) or the differential amplifier 350 output (if the S/H circuit 370 is bypassed) into a digital value that can then be read and used by the firmware 60 of the microcontroller 50 of FIG. 1.

Based on this value reported by the ADC 410, and knowing the amount of stimulation current between the two channels and the point in time at which the sample was taken, the microcontroller 50 can calculate an impedance value between the two desired channels. In an embodiment, the ADC 410 is implemented as a portion of the microcontroller, and may not be on the same Integrated Circuit chip as the rest of the impedance measurement device 300. In another embodiment, the ADC 410 may be a standalone device.

Although the examples given so far involve voltages that are all above ground, such as would be used in a device with positive power supplies only, this should not be taken as limiting. Embodiments could just as well use signals with a voltage range both above and below ground.

The present disclosure allows making impedance measurements between selected channels during active stimulation. In doing so, the present disclosure offers advantages over existing devices, it being understood that different embodiments may offer other advantages, and that no particular advantage is required for all embodiments. One of the advantages is prompt detection of problems associated with the neurostimulator device 20. Real-time impedance measurement during active stimulation means that the health of the lead wires, electrodes, and electrode-to-tissue interface is constantly monitored. If unusual changes in the impedance are detected over a short period of time, the neurostimulator device 20 can shut off stimulation (if necessary) and notify the user of an impedance error condition. This type of internal diagnostic will prevent the patient from being exposed to dangerous conditions such as long-term stimulation from an exposed broken leadwire.

With its ability to sample the impedance at precise times, the S/H circuit 370 also helps extract information regarding the health of the channel components. As discussed above, the impedance between channels is complex, which includes a real portion from a resistive component and an imaginary portion from an inductive or capacitive component. For example, the lead wires of the channels have resistance and inductance. There is channel-to-channel capacitance, and the electrode-to-tissue interface is also capacitive. It is known that for a pure resistor, current neither leads nor lags voltage; for a pure capacitor, current leads voltage by 90 degrees; and for a pure inductor, current lags voltage by 90 degrees. For a current pulse (e.g., a sinusoidal current pulse), the voltage waveforms that appear between channels can be sampled at various times, for example at two points that are 90 degrees (quarter wave) apart. The phase relationship between the current pulse and the sampled voltage pulse helps extract information regarding the complex aspects of the impedance. For example, if the current pulse leads the sampled voltage, then there is a capacitive component in the impedance.

Once the complex impedance is ascertained, it is possible to determine whether the tissue being stimulated is healthy, whether a leadwire break is imminent, or where along the leadwire a break has occurred. Prompt detection of such problems will reduce the likelihood of exposing the patient to dangerous stimulation conditions.

Another advantage offered by the present disclosure is reduced pain or discomfort for the patient. As discussed above, existing neurostimulators require the stimulation to be turned off to perform diagnostic impedance measurements. When stimulation is turned off, the patient is once again exposed to pain that was previously treated by the stimulation. In addition, the low amplitude diagnostic test signals may cause some level of discomfort to the patient as well. In comparison, when impedance measurements are made as described in this disclosure, the stimulation is ongoing during measurement. Hence, the patient feels no additional pain or discomfort.

Yet another advantage offered by the present disclosure is that the stimulation parameters can be adjusted as a function of the measured impedance during active stimulation. As patients move, such as from lying down to standing up, the electrodes may move with respect to the target tissue. The impedance measurement device 300 of the present disclosure, if programmed properly, detects changes in impedance as the electrodes move inside the patient's body during active stimulation. The microcontroller 50 can be designed and programmed to automatically adjust the stimulation parameters to compensate for the impedance changes. This means the patient himself need not manually adjust the stimulation parameters during significant changes in posture or positioning.

One more advantage offered by the present disclosure relates to better power consumption efficiency. Previous neurostimulator devices may need to use a power supply (e.g., a voltage supply) that is running at a level higher than necessary, because previous neurostimulator devices lack the ability to instantananeously detect the impedance between channels. In other words, the previous neurostimulators may need to give their respective power supplies a very high margin so as to account for impedance changes. Here, because any impedance changes can be promptly detected, the power supply can be set at a level that is just high enough to deliver the desired amount of current in response to the detected impedance. Thus, it is no longer necessary to set the power supply at a high level just to create sufficient margin to account for unexpected impedance swings. Instead, any impedance changes can be automatically accounted for by adjusting the power (e.g., voltage) accordingly. In this manner, power that would have been otherwise wasted is now conserved, thereby improving power consumption efficiency.

Figure 3:
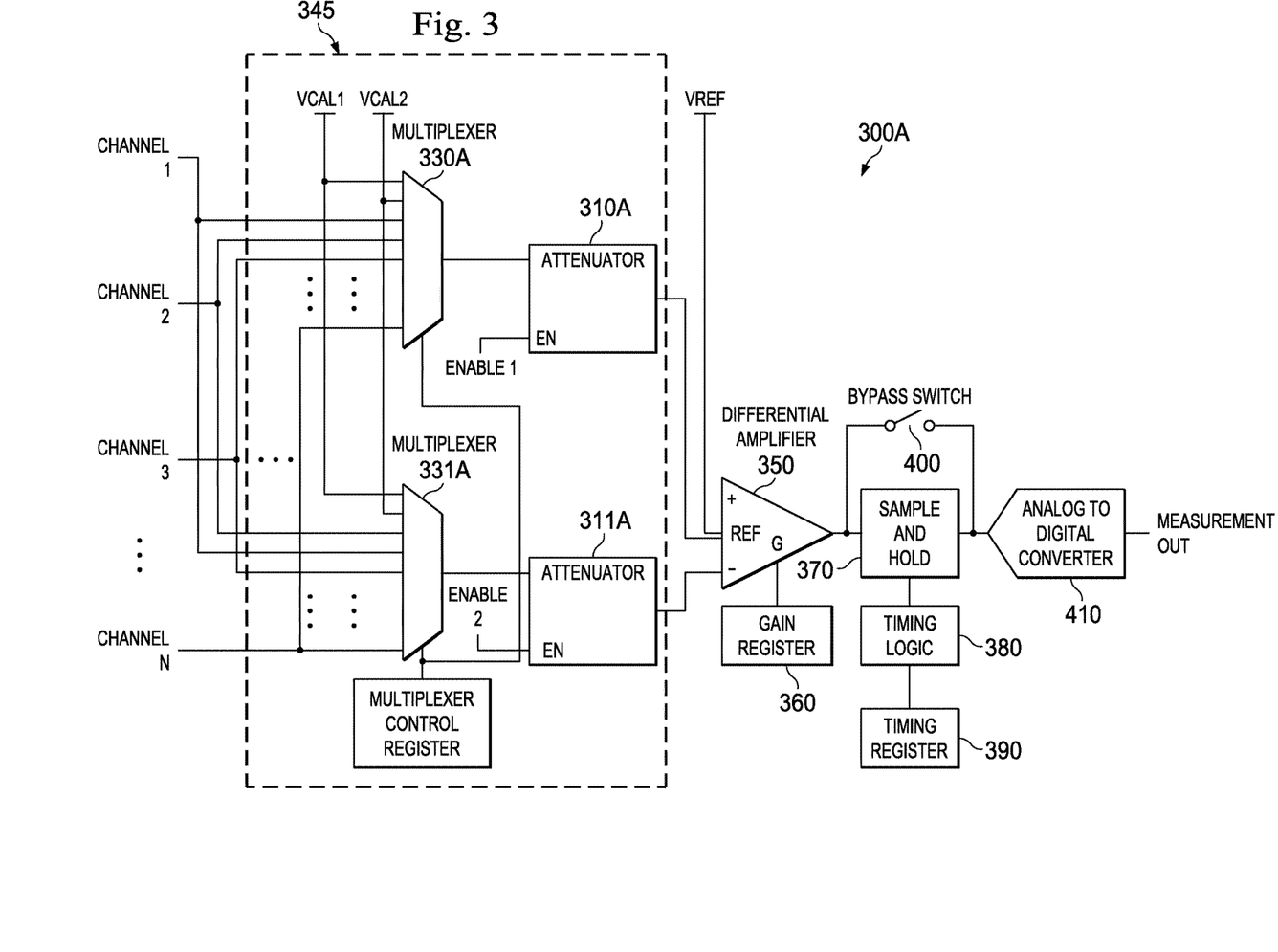
FIG. 3 is a simplified circuit level view of another embodiment of an impedance measurement device.

FIG. 3 shows a simplified diagrammatic view of an alternative embodiment of the impedance measurement device discussed above with reference to FIG. 2. The alternative embodiment of the impedance measurement device in FIG. 3 is labeled with reference numeral 300A.

Also, for the sake of clarity and consistency, similar components in both FIGS. 2 and 3 are labeled the same. Referring to FIG. 3, the first stage circuitry 345 still includes a multiplexing stage containing multiplexers 330A-331A and an attenuation stage containing attenuators 310A-311A. However, the multiplexers 330A-331A are high voltage multiplexers, meaning that they are designed to be able to handle the entire range of voltage signals outputted from the channels. In an embodiment, the multiplexers 330A-331A can accept voltages up to 25 volts. In other embodiments, the multiplexers 330A-331A can accept voltages greater than 25 volts, for example up to 50 volts or even higher. Consequently, the multiplexers 330A-331A can be coupled directly to the channels, and their outputs are then attenuated by the attenuators 310A and 311A. As is illustrated in FIG. 3, the first stage circuitry 345 only requires as many attenuators as there are multiplexers. In other words, only two attenuators 310A-311A are required here, one for each of the multiplexers 330A-331A. The remaining circuitry may be substantially identical as the embodiment shown in FIG. 2. It is understood that the embodiment shown in FIG. 3 offers substantially the same advantages as the embodiment shown in FIG. 2.

Figure 5A:
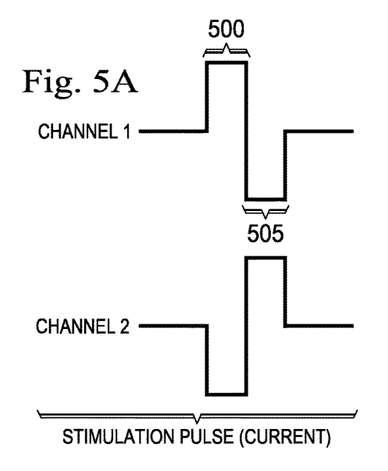
FIGS. 5A-5D are simplified waveform diagrams showing the signals of the system of FIGS. 2-3 during a typical stimulation phase.

FIGS. 5A-5D respectively depict signals, for explanatory purposes, that might be seen at various points in the circuit of FIG. 2. FIGS. 5A-5D are not drawn to scale, and the waveform shapes are approximate. FIG. 5A shows a rectangular, current-controlled stimulation pulse. For explanatory purposes, the pulse is shown on channels 1 and 2, though any combination of channels could be used. The first portion 500 of the stimulation pulse sources current on channel 1 and sinks current on channel 2, while in the second portion 505 of the pulse, channel 1 sinks and channel 2 sources current.

Figure 5B:
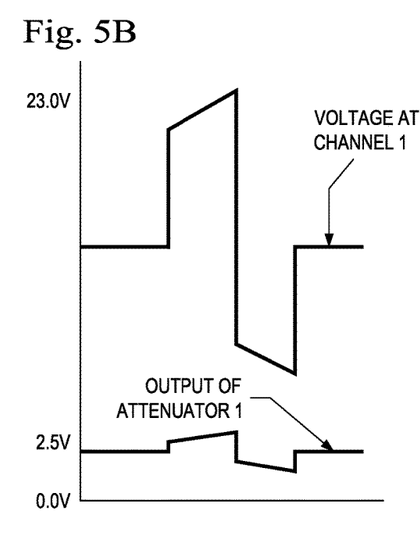
Figure 5C:
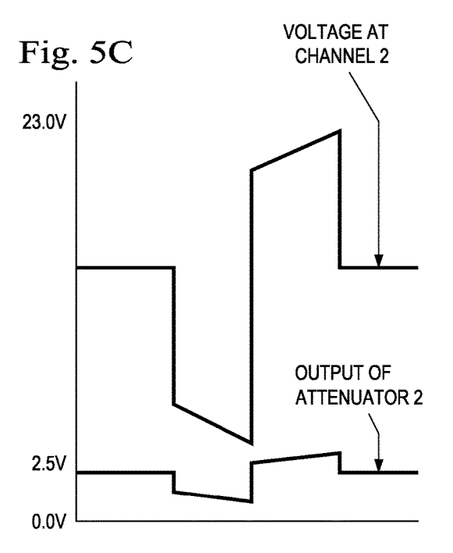

FIG. 5B shows voltage waveforms that might be seen on channel 1 and at the output of the attenuators 310 (of FIG. 2) for channel 1, with that attenuator enabled, and FIG. 5C shows the voltage waveforms that might be seen on channel 2 and at the output of the attenuators 311 (of FIG. 2) for channel 2, with that attenuator enabled. The voltage can be observed to have sharp vertical steps in response to the rectangular current pulse, which is caused by the current flow through the resistive component of the measured impedance. It can also be observed to have gradually rising and falling portions. These portions have their gradual behavior in response to reactive components of the measured impedance, and especially in response to series capacitance incorporated in the protection circuitry 90 (of FIG. 1). The output from the attenuators for the It is important to note that the voltage waveforms observed will vary substantially depending on the characteristics of the protection circuitry, lead wires, electrodes, and tissue. The waveforms depicted here are for illustration only.

Figure 5D:
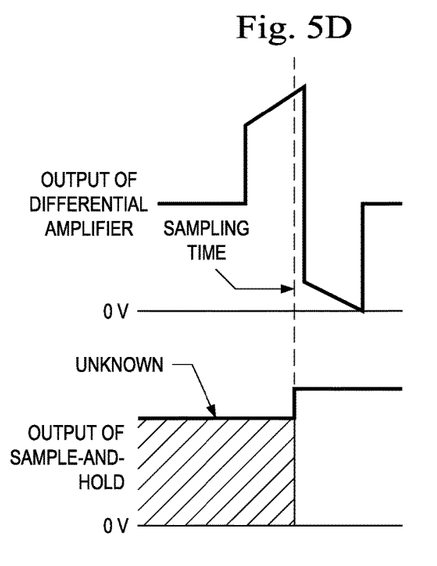

The top half of FIG. 5D shows the output of the differential amplifier 350 (of FIG. 2), with the multiplexer 330 (of FIG. 2) configured to connect channel 1 to the differential amplifier's non-inverting input and multiplexer 331 configured to connect channel 2 to the differential amplifier's inverting input. The top half of FIG. 5D also illustrates the offset added by the Vref input by showing that the amplifier output voltage is above ground throughout the pulse.

The bottom half of FIG. 5D illustrates the output of the Sample And Hold 370 (of FIG. 2). The output voltage of the sample-and-hold 370 is unknown and irrelevant until the moment of the sampling time, as controlled by the Timing Register 390 (of FIG. 2) and Timing Logic 380 (of FIG. 2). At the moment of the sampling time, the output of the sample-and-hold 370 becomes equal to the output of the differential amplifier, and that voltage is held for a sufficient period of time to allow measurement of the voltage by the Analog to Digital Converter 410 (of FIG. 2).

Figure 6:
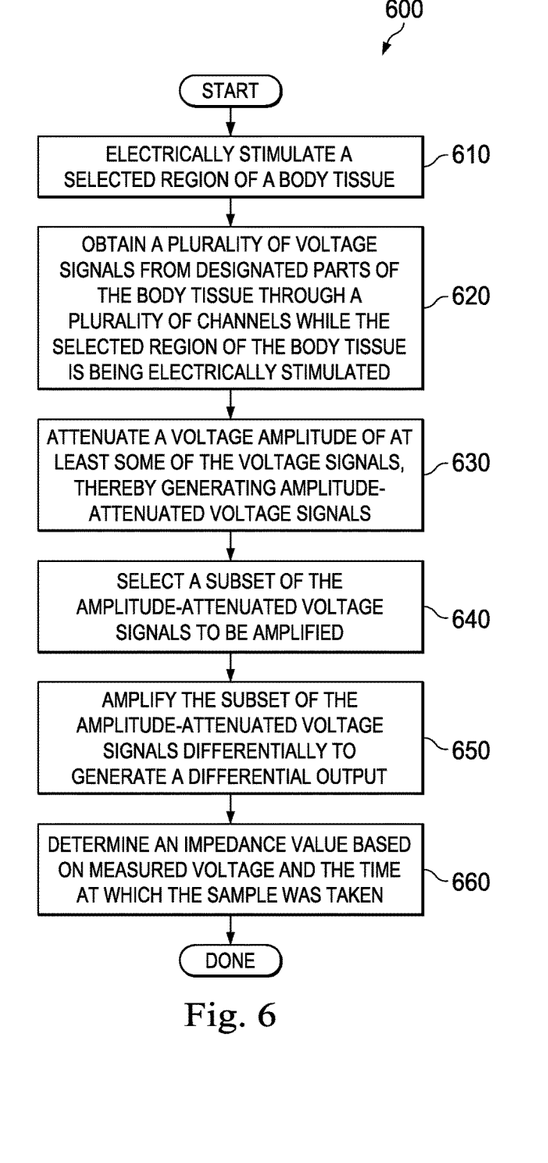
FIG. 6 is a flowchart illustrating a method of measuring impedance according to various aspects of the present disclosure.

FIG. 6 illustrates a flowchart of a method 600 involving the neurostimulator device 20. The method 600 includes block 610 in which a selected region of a body tissue is electrically stimulated. The method 600 includes block 620 in which a plurality of voltage signals is obtained from designated parts of the body tissue through a plurality of channels while the selected region of the body tissue is being electrically stimulated. The method 600 includes block 630 in which a voltage amplitude of at least some of the voltage signals is attenuated, thereby generating amplitude-attenuated voltage signals. The method 600 includes block 640 in which a subset of the amplitude-attenuated voltage signals to be amplified is selected. The method 600 includes block 650 in which the subset of the amplitude-attenuated voltage signals is amplified differentially to generate an amplifier output. The method 600 includes block 660 in which an impedance value is determined based on the measured voltage and the time at which the sample was taken.

Once the impedance is determined, a plurality of different tasks can be performed based on the value of the impedance. For example, if the impedance value falls within a first predefined range, it means the neurostimulator device is functioning normally, and electrical stimulation may continue without notifying the user. If the impedance value falls outside of the first predefined range but is within a second predefined range, it may mean that certain stimulation parameters may need to be adjusted. The amount of electrical current used for stimulation may be automatically increased or decreased, for example, and the stimulation may still continue. The user may or may not be notified. If the impedance value falls outside of the second predefined range but is within a third predefined range, the neurostimulator may notify the user of an abnormality, who may then decide to suspend stimulation and consult with a doctor, or continue stimulation after manually adjusting certain parameters of the stimulator. If the impedance value falls outside the third predefined range, then it may mean that the neurostimulator is malfunctioning. The neurostimulator may immediately discontinue the stimulation and notify the user as such. It is understood that the above tasks are merely examples, and that other suitable tasks may be performed in response to the measured impedance value.

Figure 7A:
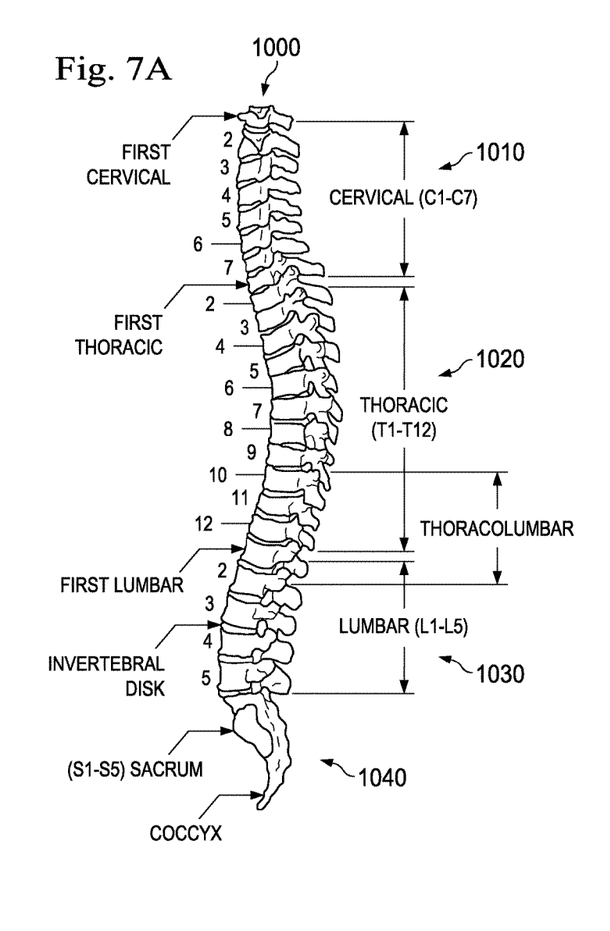
FIGS. 7A and 7B are side and posterior views of a human spine, respectively.
Figure 7B:
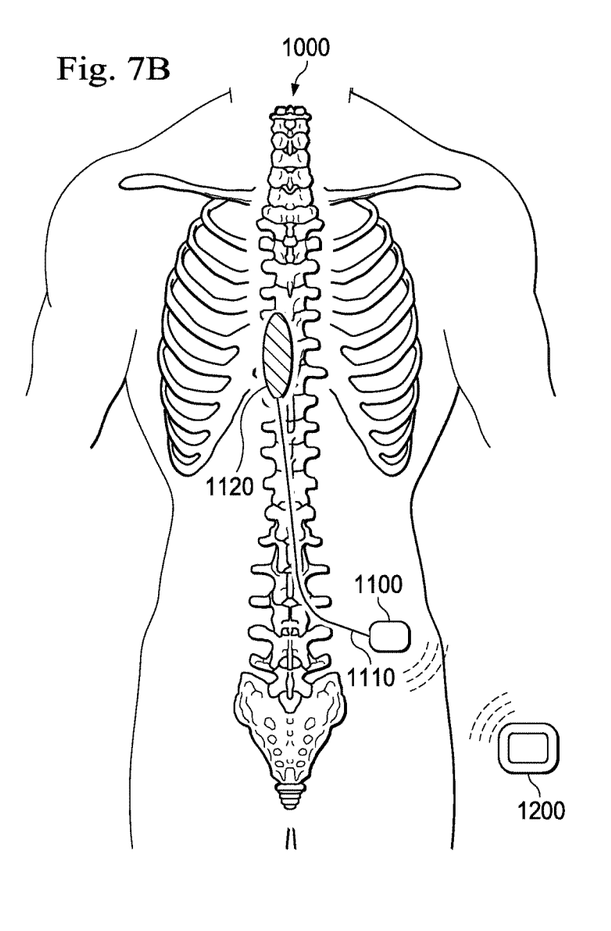

FIG. 7A is a side view of a spine 1000, and FIG. 7B is a posterior view of the spine 1000. The spine 1000 includes a cervical region 1010, a thoracic region 1020, a lumbar region 1030, and a sacrococcygeal region 1040. The cervical region 1010 includes the top 7 vertebrae, which may be designated with C1-C7. The thoracic region 1020 includes the next 12 vertebrae below the cervical region 1010, which may be designated with T1-T12. The lumbar region 1030 includes the final 5 "true" vertebrae, which may be designated with L1-L5. The sacrococcygeal region 1040 includes 9 fused vertebrae that make up the sacrum and the coccyx. The fused vertebrae of the sacrum may be designated with S1-S5.

Neural tissue (not illustrated for the sake of simplicity) branch off from the spinal cord through spaces between the vertebrae. The neural tissue can be individually and selectively stimulated in accordance with various aspects of the present disclosure. For example, referring to FIG. 7B, an IPG device 1100 is implanted inside the body. The IPG device 1100 may include various embodiments of the neurostimulator device 20 described above. A conductive lead 1110 is electrically coupled to the circuitry inside the IPG device 1100. The conductive lead 1110 may be removably coupled to the IPG device 1100 through a connector, for example. A distal end of the conductive lead 1110 is attached to one or more electrodes 1120. The electrodes 1120 are implanted adjacent to a desired nerve tissue in the thoracic region 1020. Using well-established and known techniques in the art, the distal end of the lead 1110 with its accompanying electrodes may be positioned along or near the epidural space of the spinal cord. It is understood that although only one conductive lead 1110 is shown herein for the sake of simplicity, more than one conductive lead 1110 and corresponding electrodes 1120 may be implanted and connected to the IPG device 1100.

The electrodes 1120 deliver current drawn from the current sources in the IPG device 1100, therefore generating an electric field near the neural tissue. The electric field stimulates the neural tissue to accomplish its intended functions. For example, the neural stimulation may alleviate pain in an embodiment. In other embodiments, a stimulator as described above may be placed in different locations throughout the body and may be programmed to address a variety of problems, including for example but without limitation: prevention or reduction of epileptic seizures, weight control or regulation of heart beats.

It is understood that the IPG device 1100, the lead 1110, and the electrodes 1120 may be implanted completely inside the body, may be positioned completely outside the body or may have only one or more components implanted within the body while other components remain outside the body. When they are implanted inside the body, the implant location may be adjusted (e.g., anywhere along the spine 1000) to deliver the intended therapeutic effects of spinal cord electrical stimulation in a desired region of the spine. Furthermore, it is understood that the IPG device 1100 may be controlled by a patient programmer or a clinician programmer 1200.

The IPG device 1100 may be set in a trialing mode to test different groups of stimulation patterns. For example, in an embodiment, a paddle-style lead is used as a lead to stimulate the neural tissue. The paddle-style lead has a plurality of electrodes that can each be programmably set as a cathode or an anode. The patient or the clinician may programmably enter a first stimulation pattern, in which a subset of electrodes on the lead are designated as cathodes, and a different subset of electrodes on the lead are designated as anodes. The current flow between the anodes and the cathodes serves to electrically stimulate a desired adjacent area of neural tissue by generating an electric field in the tissue. The selection of the cathode and anode subset may be made to minimize electric field leakage and thus reduce stimulation of undesired areas of neural tissue.

The patient may then decide to try a second stimulation pattern that is different from the first stimulation pattern. The second stimulation pattern sets different groups of electrodes as anodes and cathodes than the first stimulation pattern. The cathodes of the second stimulation pattern will carry out electrical stimulation of a different area of the neural tissue. The patient may decide whether the first stimulation pattern or the second stimulation pattern is better. He may also try an additional number of different stimulation patterns until he finds the one he prefers.

The present disclosure describes a means for measuring the impedance between channels during active stimulation, allowing the neurostimulator device to perform this function during normal therapy delivery without requiring the suspension of stimulation or the need for special diagnostic modes for measuring impedance.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method, comprising:
electrically stimulating a selected region of a body tissue;
obtaining a plurality of voltage signals from designated parts of the body tissue while the selected region of the body tissue is being electrically stimulated;
attenuating a voltage amplitude of at least some of the voltage signals, thereby generating amplitude-attenuated voltage signals;
selecting a subset of the amplitude-attenuated voltage signals to be amplified;
amplifying the subset of the amplitude-attenuated voltage signals differentially to generate an amplifier output; and
determining an impedance associated with the selected region of the body tissue based on the amplifier output.

2. The method of claim 1, wherein the electrically stimulating includes electrically stimulating the selected region of the body tissue with a plurality of implantable electrodes.

3. The method of claim 1, wherein the attenuating is carried out using a plurality of voltage attenuators that are each coupled to a respective one of the plurality of voltage signals;
and wherein each of the voltage attenuators is operable to be put in one of an "on" state and an "off" state in response to a control signal.

4. The method of claim 1, wherein the selecting includes routing the amplitude-attenuated voltage signals through one or more multiplexers in response to a control signal;
and wherein the subset of the amplitude-attenuated voltage signals includes outputs of the one or more multiplexers.

5. The method of claim 4, further including performing a calibration process that includes sending a calibration signal to the one or more multiplexers.

6. The method of claim 1, further including adding a reference signal to the amplifier output.

7. The method of claim 1, further including taking multiple samples of the amplifier output, wherein each sample is taken at a respective programmably-determined point in time.

8. The method of claim 7, wherein the determining the impedance includes calculating an imaginary component of the impedance based on the multiple samples.

9. The method of claim 1, wherein at least one of the attenuating, the selecting, the amplifying, and the determining is carried out at least in part using a microcontroller.

10. The method of claim 1, further including performing one of a plurality of tasks in response to the determined impedance, wherein the plurality of tasks each correspond to a range of impedance values within which the determined impedance falls.

11. The method of claim 10, wherein the plurality of tasks are selected from the group consisting of: continuing the electrically stimulating, continuing the electrically stimulating after adjusting parameters associated with the electrically stimulating, notifying the user of an abnormality and waiting for user input before continuing the electrically stimulating, and discontinuing the electrically stimulating immediately and notifying the user of a malfunction.

12. A method, comprising:
delivering electrical pulses to a patient;
receiving a plurality of voltage signals from a selected body region of the patient in response to the delivering;
generating amplitude-attenuated voltage signals by attenuating a voltage amplitude of at least some of the voltage signals;
amplifying a subset of the amplitude-attenuated voltage signals differentially, thereby producing a differential output; and
calculating an impedance associated with the selected body region based on the differential output.

13. The method of claim 12, wherein the attenuating comprises attenuating the voltage amplitude using a plurality of programmable voltage attenuators that can be individually turned on or off.

14. The method of claim 12, wherein the amplifying comprises routing at least some of the voltage signals through one or more multiplexors.

15. The method of claim 14, further comprising calibrating the one or more multiplexors.

16. The method of claim 12, further comprising applying a reference signal to the differential output.

17. The method of claim 12, wherein the calculating comprises:
sampling the differential output at a plurality of predetermined points in time; and calculating the impedance in response to the sampling.

18. The method of claim 12, wherein the delivering and the calculating are performed simultaneously.

19. The method of claim 12, wherein the impedance is determined while electrical stimulation is applied.

20. A method, comprising:
electrically stimulating a selected region of a body tissue with a plurality of implantable channels;
obtaining a plurality of voltage signals from designated parts of the body tissue while the selected region of the body tissue is being electrically stimulated;
attenuating, using a plurality of voltage attenuators that are each associated with a respective one of the plurality of voltage signals, a voltage amplitude of at least some of the voltage signals, thereby generating amplitude-attenuated voltage signals;
selecting a subset of the amplitude-attenuated voltage signals to be amplified;
amplifying the subset of the amplitude-attenuated voltage signals differentially to generate an amplifier output;
taking multiple samples of the amplifier output; and
determining an impedance associated with the selected region of the body tissue based on the amplifier output, including calculating an imaginary component of the impedance based on the multiple samples.

* * * * *